United States Patent [19]

Fleming

[11] Patent Number: Plant 7,452

[45] Date of Patent: Feb. 19, 1991

[54] KALANCHOE PLANT NAMED CONTENDER

[75] Inventor: Margaret M. Fleming, Soquel, Calif.

[73] Assignee: The Plant Company, Soquel, Calif.

[21] Appl. No.: 421,679

[22] Filed: Oct. 16, 1989

[51] Int. Cl.[5] ..... A01H 5/00
[52] U.S. Cl. ..... Plt./68
[58] Field of Search ..... Plt./68

*Primary Examiner*—Howard J. Locker
*Attorney, Agent, or Firm*—Foley & Lardner, Schwartz, Jeffery, Schwaab, Mack, Blumenthal & Evans

[57] ABSTRACT

A Kalanchoe plant named Contender particularly characterized by its red flower color; flower diameter of 17 to 19 mm at maturity; flowering response of from 10 weeks in summer to 12 weeks in winter after start of short days; very floriferous with excellent display of many flowers; excellent keeping quality of flowers and foliage; branches freely with or without pinching; intermediate vigor; responsiveness to B-9 applications to reduce internode length and peduncle elongation; and adaptability to pot sizes from 10 to 15 cm.

2 Drawing Sheets

The present invention relates to a new and distinctive cultivar of Kalanchoe plant, botanically known as *Kalanchoe blossfeldiana* Poelln., and referred to by the cultivar name Contender.

Contender, identified as 542-004, is a product of a planned breeding program which had the objective of creating new Kalanchoe cultivars for year-round commercial production, with earlier flowering response, good branching yet compact habit, suitable for flowering in pots ranging from 10 to 15 cm, and with good flower and foliage keeping quality.

Contender was originated from a cross by the inventor Margaret M. Fleming in a controlled breeding program in Half Moon Bay, Calif., in 1984.

The female parent of Contender was the cultivar Caliente, disclosed in U.S. Plant Pat. No. 5,669. The male parent was a seedling identified as 403-253, and now referred to by the varietal designation Western Red, disclosed in a pending plant patent application of the present inventor.

Contender was discovered and selected by the inventor as one flowering plant within the progeny of the stated cross in February, 1986 in a controlled enviornment in Soquel, Calif.

The first act of asexual reproduction of Contender was accomplished when vegetative cuttings were taken by the inventor from the initial selection in July, 1986 in a controlled environment in Soquel, Calif.

Horticultural examination of controlled flowerings of successive plantings has shown that the unique combination of characteristics as herein disclosed for Contender are firmly fixed and are retained through successive generations of asexual reproduction. Contender has not been observed under all possible environmental conditions. The phenotype may vary significantly with variations in environment such as temperature, light intensity and daylength.

The following observations, measurements and comparisons describe plants grown in Soquel, Calif., under greenhouse conditions which approximate those generally used in commercial greenhouse practice.

The following traits have been repeatedly observed and are determined to be basic characteristics of Contender, which, in combination, distinguish this Kalanchoe as a new and distinct cultivar.

1. Red flower color.
2. Flower diameter of 17 to 19 mm at maturity.
3. Flowering response to from 10 weeks in summer to 12 weeks in winter after start of short days.
4. Very floriferous with excellent display of many flowers.
5. Excellent keeping quality of flowers and foliage.
6. Branches freely with or without pinching.
7. Intermediate vigor.
8. Responds well to B-9 applications to reduce internode length and peduncle elongation.
9. Proper scheduling makes this new cultivar suitable for production in 10 cm to 15 cm pots.

The accompanying photographic drawings show typical inflorescence and leaf characteristics of Contender, with colors being as nearly true as possible with illustrations of this type. Sheet 1 is a color photograph of Contender grown as a non-pinched flowering Kalanchoe in a 10 cm pot. Although the leaf edges appear to have a dark or reddish tone, this is a photographic imperfection and not a characteristic of Contender. Sheet 2 is a black and white photograph showing the leaves of Contender at three stages of development (mature, intermediate and immature).

Of the commercial cultivars known to the inventor, several may be compared to Contender in separate characteristics; in total no single commercial cultivar compares. Contender is similar to Attraction, disclosed in U.S. Plant Pat. No. 5,888, in flower size and flowering response. The flower color of Contender is bright red, while Attraction has a more brick red flower color. Contender also has much better keeping quality of both flowers and foliage than Attraction. In comparison to Pollux, disclosed in U.S. Plant Pat. No. 4,816, Contender has larger flowers, is more floriferous with a better display of more flowers, is more productive as a stock plant in production of vegetative cuttings, has a faster flowering response by two to three weeks, and has better resistance to mildew than Pollux. Contender and Pollux are similar to flower color.

Contender can also be compared to the parent cultivars Caliente and Western Red. With regard to the female parent Caliente, leaf form and flowering response for both are similar. Contender is intermediate in height, which Caliente is taller. Contender has smaller foliage which is a darker green in color, and the flower color of Contender is a more deep and intense red.

Compared to the male parent Western Red, the flower color of Contender is a deeper red and the flower diameter is larger. The flowers of both cultivars are non-fading. Contender is shorter than Western Red under the same growing conditions, and has a different foliage form.

In the following description color references are made to The Royal Horticultural Society Colour Chart. The color values were determined on plant material grown as a non-pinched pot plant in a 10. cm pot in Soquel, Calif., on Oct. 23, 1988.

Classification:

*Botanical.*—*Kalanchoe blossfeldiana* Poelln. cv. Contender.

*Commercial.*—Flowering pot Kalanchoe.

Parentage:

*Female parent.*—Caliente (U.S. Plant Pat. No. 5,669).

*Male parent.*—Seedling 403-253, now referred to as Western Red.

Propagation:

(A) *Type cutting.*—Short tip cutting, with stems up to 2 cm.

(B) *Time to root.*—10 days at 21° C. in summer, 14 days at 21° C. in winter.

(C) Rooting habit.—Many very fine roots, fibrous.

Plant description:

(A) *Form.*—Intermediate, upright growth. Growing and scheduling practices can produce a small plant in a 10 cm pot up to larger plants in a 15 cm pot.

(B) *Habit of growth.*—Rate of growth moderate for this type of plant. Generally, shoots are formed at every node; internode length of natural vegetative plant, 12–25 mm.

(C) *Height.*—Medium, 15–25 cm. above a 10 cm. pot, with 2–3 applications of 3500 ppm B-9 SP linear growth regulator.

(D) *Foliage description.*—Leaves simple, opposite, slightly lobed. 1. Size: Average full grown leaf in a 10 cm flowering pot is 110 mm long×60 mm wide. 2. Shape: Ovate to elliptic, apex obtuse to slightly pointed, base attenuate. 3. Texture: Glabrous, coriaceous, succulent. 4. Margin: Sinuate to crenate. 5. Color: Mature foliage: Upper surface 147A. Under surface 147B. 6. Durability: Excellent; no degradation observed even on the lower foliage of plants retained for months beyond normal expectancy.

Flowering description:

(A) *Flowering habit.*—Inflorescence of each shoot is formed by dichotomous branching, starting with opening of terminal flower of main axis, followed by terminal flowers of the side branches, continuing with subsequent development of branches in the inflorescence. Opening of new buds (12–19 mm. in length) will continue for two months or more. Individual flowers last two weeks or more after opening.

(B) *Flowering response.*—Flowering time under controlled daylength after start of short days is 10 weeks in summer to 12 weeks in winter.

(C) *Flowers borne.*—Compound dichasial cymes; peduncle length is 5–12 cm. in length and 4–8 mm. in diameter, depending on growing conditions and application of growth regulator; pedicels 5–7 mm. in length and slightly greater than 1 mm. in diameter.

(D) *Quantity of flowers.*—Very floriferous, on both main axis and side laterals; typical floret count of 80–100 per major inflorescence and 400–500 total per plant in a 10 cm. pot grown in accordance with commercial culture practices; 4 to 6 side laterals in a 10 cm pot.

(E) *Petals.*—1. Shape: Slightly pointed to almost round. 2. Color: Upper surface: 44A to 44B. Under surface: Base 38A, streaked with 43B. 3. Number of petals: 4, united in corolla. 4. Flower diameter: 17 to 19 mm at maturity.

(F) *Reproductive organs.*—1. Stamens: 8 in number. a. Anther shape: Flat, elliptical, color yellow. b. Filament color: Light green. c. Pollen color: Yellow. 2. Pistils a. Stigma shape: Flat, crystalline, color greenish white. b. Style color: Light green. c. Ovaries: 4-celled, color light green.

(G) *Keeping quality.*—Excellent; flowers last more than two weeks or more, with the plant being in flower two months or more. Observations to date indicate that Contender may be the longest lasting red Kalanchoe presently commercially available.

Disease resistance: Contender is susceptible to the foliar disease Powdery Mildew on the same level as several other commercial cultivars, that is, if the inoculum is present and conditions for infection exist, Contender is susceptible. To data, no occurrences of chlorosis, necrotic spot, tip die-back, root rot, or stem rot have been observed. Contender is resistant or immune to the flower disease Botrytis, and no fading or color breaking has been observed.

Fragrance: Non perceived in flowers or foliage.

I claim:

1. A new and distinct plant of Kalanchoe named Contender, as described and illustrated.

* * * * *

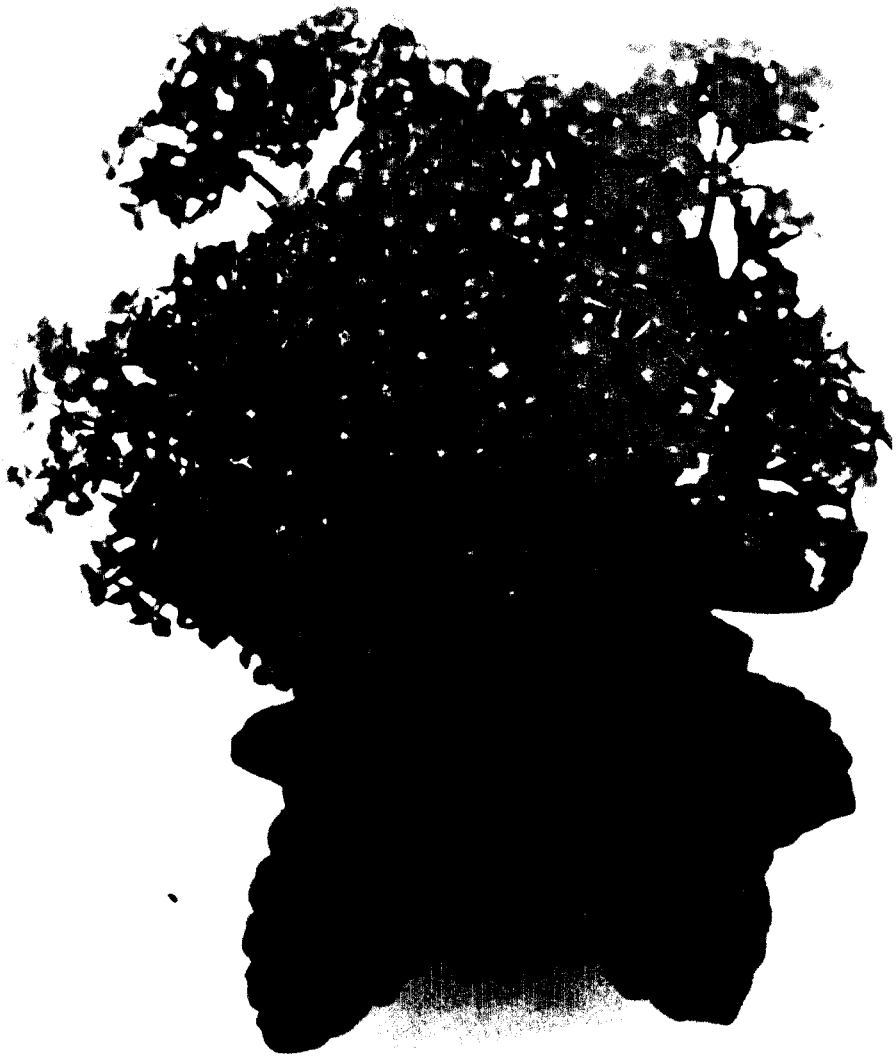

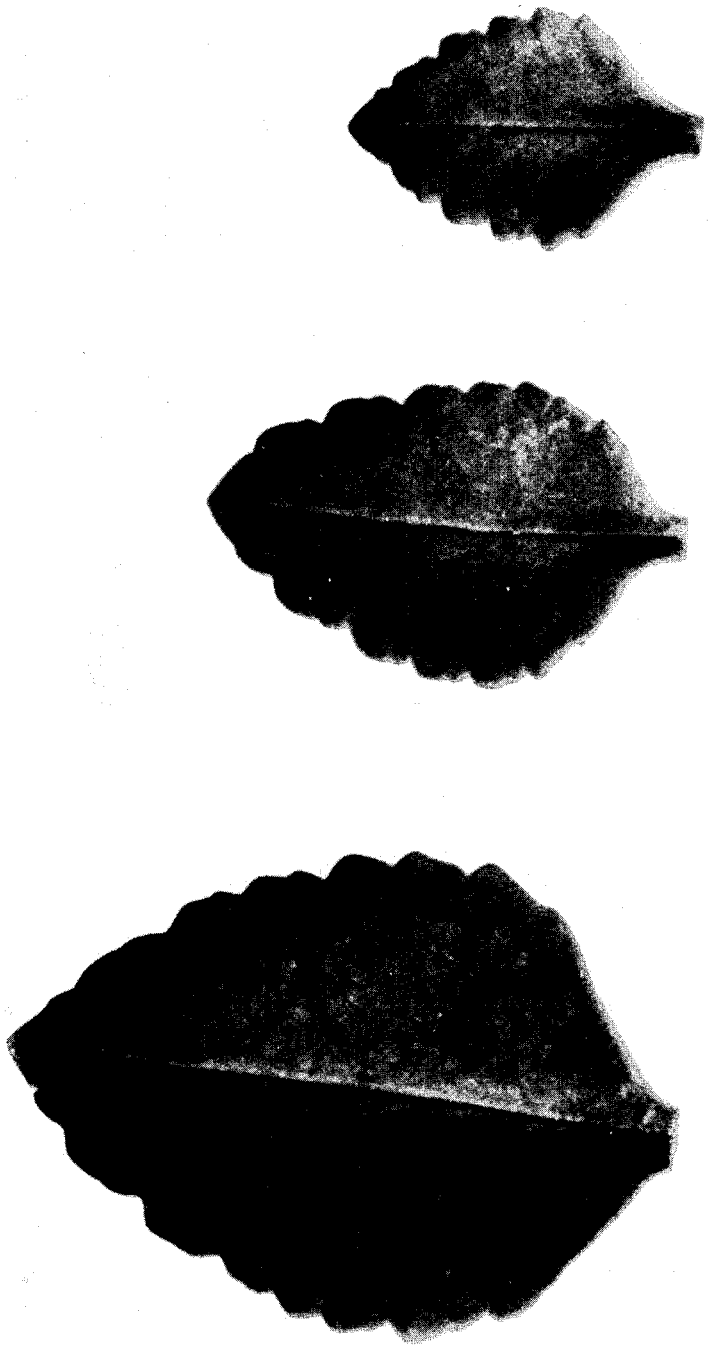
CONTENDER